US005770531A

United States Patent [19]
Sudduth et al.

[11] Patent Number: 5,770,531
[45] Date of Patent: Jun. 23, 1998

[54] MECHANICAL AND INTERNAL SOFTENING FOR NONWOVEN WEB

[75] Inventors: Gregory Todd Sudduth, Lawrenceville; Ali Yahiaoui, Roswell, both of Ga.

[73] Assignee: Kimberly—Clark Worldwide, Inc., Neenah, Wis.

[21] Appl. No.: 639,637

[22] Filed: Apr. 29, 1996

[51] Int. Cl.[6] ................................................ B32B 23/16
[52] U.S. Cl. ........................ 442/361; 442/381; 442/382; 442/392; 442/414
[58] Field of Search ................................. 442/361, 381, 442/382, 392, 414

[56]  References Cited

U.S. PATENT DOCUMENTS

| | | | |
|---|---|---|---|
| 3,338,992 | 8/1967 | Kinney | 264/24 |
| 3,341,394 | 9/1967 | Kinney | 161/72 |
| 3,502,763 | 3/1970 | Hartman | 264/210 |
| 3,542,615 | 11/1970 | Dobo et al. | 156/181 |
| 3,692,618 | 9/1972 | Dorschner et al. | 161/72 |
| 3,802,817 | 4/1974 | Matsuki et al. | 425/66 |
| 3,849,241 | 11/1974 | Butin et al. | 161/169 |
| 3,855,046 | 12/1974 | Hansen et al. | 161/150 |
| 4,041,203 | 8/1977 | Brock et al. | 428/157 |
| 4,088,731 | 5/1978 | Groome | 264/282 |
| 4,100,324 | 7/1978 | Anderson et al. | 428/288 |
| 4,340,563 | 7/1982 | Appel et al. | 264/518 |
| 4,374,888 | 2/1983 | Bornslaeger | 428/198 |
| 4,443,513 | 4/1984 | Meitner et al. | 422/195 |
| 4,735,849 | 4/1988 | Murakami et al. | 428/224 |
| 4,795,668 | 1/1989 | Krueger et al. | 428/174 |
| 4,806,300 | 2/1989 | Walton et al. | 264/288 |
| 4,818,464 | 4/1989 | Lau | 264/510 |
| 4,919,877 | 4/1990 | Parsons et al. | 264/282 |
| 4,923,914 | 5/1990 | Nohr et al. | 524/99 |
| 4,965,122 | 10/1990 | Morman | 428/225 |
| 4,981,747 | 1/1991 | Morman | 428/198 |
| 5,041,255 | 8/1991 | Zafiroglu | 264/288.8 |
| 5,057,368 | 10/1991 | Largman et al. | 428/397 |
| 5,069,970 | 12/1991 | Largman et al. | 428/373 |
| 5,108,820 | 4/1992 | Kaneko et al. | 428/198 |
| 5,114,781 | 5/1992 | Morman | 428/198 |
| 5,145,727 | 9/1992 | Potts et al. | 428/198 |
| 5,169,706 | 12/1992 | Collier, IV et al. | 428/152 |
| 5,178,931 | 1/1993 | Perkins et al. | 428/198 |
| 5,188,885 | 2/1993 | Timmons et al. | 428/198 |
| 5,244,482 | 9/1993 | Hassenboehler, Jr. et al. | 55/528 |
| 5,277,976 | 1/1994 | Hogie et al. | 428/397 |
| 5,336,552 | 8/1994 | Strack et al. | 428/224 |
| 5,382,400 | 1/1995 | Pike et al. | 264/168 |
| 5,413,811 | 5/1995 | Fitting et al. | 427/176 |
| 5,466,410 | 11/1995 | Hills | 264/172.11 |
| 5,482,765 | 1/1996 | Bradley et al. | 428/286 |

FOREIGN PATENT DOCUMENTS

2513251 A1  9/1976  Germany .......................... D01F 8/08

OTHER PUBLICATIONS

Riggs, C. L., and Sherill, J. C., Textile Laundering Technology, 1979, p. 71–74.
American Dyestuff Reporter, Sep. 1973, p. 24–26.
Textile World, Dec. 1973, p. 45–46.

Primary Examiner—Marion E. McCamish
Assistant Examiner—Elizabeth M. Cole
Attorney, Agent, or Firm—James B. Robinson; William D. Herrick

[57] ABSTRACT

There is provided a web which has been spun from a mixture of thermoplastic polymer and a softening additive in an amount up to about 3 weight percent, and which has been mechanically treated to increase softness. The web has a final cup crush value which is less than 50 percent of the starting cup crush value and the drop in cup crush value is greater than the sum of the treatments individually. The web may be a single layer or may be a laminate of spunbond and other materials such as meltblown and coform fabrics.

17 Claims, 2 Drawing Sheets

MECHANICAL AND INTERNAL SOFTENING FOR NONWOVEN WEB

BACKGROUND OF THE INVENTION

This invention relates to the field of nonwoven fabrics or webs and their manufacture. More particularly, it relates to such nonwoven fabrics which are comprised of at least one layer of staple fibers or filaments or continuous filaments. Such fibers are commonly comprised of thermoplastic polymers such as polyamides, polyesters, polyethers and polyolefins such as polypropylene, polyethylene, polybutylene and copolymers and blends thereof.

Uses for such microfibrous webs are in such personal care products as diapers, training pants, feminine hygiene products and adult incontinence products, infection control products like surgical drapes, gowns and sterile wraps, and in various clothing applications. The softness of the web is an important factor in such applications as the web may be in contact with a wearer for an extended period of time.

Various methods to increase the softness of a nonwoven web are known in the art. These methods include wash softening, mechanical stretching, and topical treatment of the web with softening chemicals.

The technique of wash softening the nonwoven web is a time consuming, batch process which does not lend itself to the requirements of industrial production. In addition, large volumes of water from the washing process must be handled, either by recycling or disposal, and the web must be dried. Drying a nonwoven web is an energy consuming process which is somewhat difficult to control in a commercial setting, sometimes resulting in remelted, glazed or otherwise damaged webs.

Mechanical softening alone by stretching does not provide the degree of softness being sought for some applications. Topical treatments also do not provide the degree of softness sought for some applications and have additional manufacturing constraints.

Treatments to increase the softness of a nonwoven web involving both mechanical and chemical means are described in U.S. Pat. No. 5,413,811 to Fitting et al. This patent describes topical chemical treatments and mechanical stretching to produce a softer web by wetting a nonwoven web having a starting, unstretched width and a starting cup crush value, with an aqueous solution of softening chemicals, necking the saturated nonwoven web to a second width of between about 50 and 95 percent of its starting, unstretched width, and drying the nonwoven web at a temperature and time sufficient to remove at least 95 percent of the moisture from the nonwoven web.

While this method produces a very soft web, a simpler method would be desirable as it would have fewer steps and therefore fewer opportunities for error in manufacturing. It would also be preferable to avoid a topical treatment of the web as this is a relatively messy step in the process.

Internal, as contrasted with topical, additives for webs for the purpose, for example, of increasing the repellence of a fabric, are known in the art. These usually involve the use of a fluorocarbon additive which migrates or "blooms" to the surface of a web after fiber formation. Examples of such additives may be found in U.S. Pat. No. 5,178,931 to Perkins et al. and U.S. Pat. No. 5,482,765 to Bradley et al.

There remains a need for a web which is produced by a softening process or treatment procedure which avoids topical treatments and yet is sufficiently soft for garment applications. This process must be relatively rapid, when compared to wash softening, clean in comparison to topical treating, and suited to large scale commercial manufacturing.

Accordingly, it is an object of this invention to provide a microfibrous web which avoids topical treatment chemicals, can be produced in a continuous industrial production operation, and which is soft enough for garment applications.

SUMMARY

The objects of this invention are achieved by a web which has been spun from a mixture of thermoplastic polymer and an internal softening additive in an amount up to about 3 weight percent, and which has been mechanically treated to increase softness. The web has a final cup crush value which is less than 50 percent of the starting cup crush value and the drop in cup crush value is greater than the sum of the drop in cup crush values from the treatments individually.

DEFINITIONS

As used herein the term "nonwoven fabric or web" means a web having a structure of individual fibers or threads which are interlaid, but not in an identifiable manner as in a knitted fabric. Nonwoven fabrics or webs have been formed from many processes such as for example, meltblowing processes, spunbonding processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91).

As used herein the term "microfibers" means small diameter fibers having an average diameter not greater than about 75 microns, for example, having an average diameter of from about 0.5 microns to about 50 microns, or more particularly, microfibers may have an average diameter of from about 2 microns to about 40 microns. Another frequently used expression of fiber diameter is denier, which is defined as grams per 9000 meters of a fiber and may be calculated as fiber diameter in microns squared, multiplied by the density in grams/cc, multiplied by 0.00707. A lower denier indicates a finer fiber and a higher denier indicates a thicker or heavier fiber. For example, the diameter of a polypropylene fiber given as 15 microns may be converted to denier by squaring, multiplying the result by 0.89 g/cc and multiplying by 0.00707. Thus, a 15 micron polypropylene fiber has a denier of about 1.42, ($15^2 \times 0.89 \times 0.00707 = 1.415$). Outside the United States the unit of measurement is more commonly the "tex", which is defined as the grams per kilometer of fiber and which may be calculated as denier/9.

As used herein the term "spunbonded fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. Nos. 4,340,563 to Appel et al., and 3,692,618 to Dorschner et al., 3,802,817 to Matsuki et al., 3,338,992 and 3,341,394 to Kinney, 3,502,763 to Hartman, and 3,542,615 to Dobo et al. Spunbond fibers are generally not tacky when they are deposited onto a collecting surface. Spunbond fibers are generally continuous and have average diameters (from a sample of at least 10) larger than 7 microns, more particularly, between about 10 and 20 microns.

As used herein the term "meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin. Meltblown fibers are microfibers which may be continuous or discontinuous, are generally smaller than 10 microns in average diameter, and are generally tacky when deposited onto a collecting surface.

As used herein, the term "coform" means a process in which at least two meltblown dieheads are arranged around a central chute through which other materials are added to the web while it is forming. Such other materials may be pulp, superabsorbent particles, cellulose or staple fibers, for example. Coform processes are shown in commonly assigned U.S. Pat. Nos. 4,818,464 to Lau and 4,100,324 to Anderson et al. Webs produced by the coform process are generally referred to as coform materials.

As used herein "multilayer laminate" means a laminate wherein some of the layers are spunbond and some meltblown such as a spunbond/meltblown/spunbond (SMS) laminate and others as disclosed in U.S. Pat. Nos. 4,041,203 to Brock et al., 5,169,706 to Collier, et al, 5,145,727 to Potts et al., 5,178,931 to Perkins et al. and 5,188,885 to Timmons et al. Such a laminate may be made by sequentially depositing onto a moving forming belt first a spunbond fabric layer, then a meltblown fabric layer and last another spunbond layer and then bonding the laminate in a manner described below. Alternatively, the fabric layers may be made individually, collected in rolls, and combined in a separate bonding step. Such fabrics usually have a basis weight of from about 0.1 to 12 osy (6 to 400 gsm), or more particularly from about 0.75 to about 3 osy. Multilayer laminates may also have various numbers of meltblown layers or multiple spunbond layers in many different configurations and may include other materials like films (F) or coform materials, e.g. SMMS, SM, SFS, etc.

As used herein the term "polymer" generally includes but is not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the molecule. These configurations include, but are not limited to isotactic, syndiotactic and random symmetries.

As used herein, the term "machine direction" or MD means the length of a fabric in the direction in which it is produced. The term "cross machine direction" or CD means the width of fabric, i.e. a direction generally perpendicular to the MD.

As used herein the term "monocomponent" fiber refers to a fiber formed from one or more extruders using only one polymer. This is not meant to exclude fibers formed from one polymer to which small amounts of additives have been added for coloration, anti-static properties, lubrication, hydrophilicity, etc. These additives, e.g. titanium dioxide for coloration, are generally present in an amount less than 5 weight percent and more typically about 2 weight percent.

As used herein the term "conjugate fibers" refers to fibers which have been formed from at least two polymers usually extruded from separate extruders but spun together to form one fiber. Conjugate fibers are also sometimes referred to as multicomponent or bicomponent fibers. The polymers are usually different from each other though conjugate fibers may be monocomponent fibers. The polymers is are arranged in substantially constantly positioned distinct zones across the cross-section of the conjugate fibers and extend continuously along the length of the conjugate fibers. The configuration of such a conjugate fiber may be, for example, a sheath/core arrangement wherein one polymer is surrounded by another or may be a side by side arrangement, a pie arrangement or an "islands-in-the-sea" arrangement. Conjugate fibers are taught in U.S. Pat. Nos. 5,108,820 to Kaneko et al., 4,795,668 to Krueger et al. and 5,336,552 to Strack et al. Conjugate fibers are also taught in U.S. Pat. No. 5,382,400 to Pike et al. and may be used to produce crimp in the fibers by using the differential rates of expansion and contraction of the two (or more) polymers. Crimped fibers may also be produced by mechanical means and by the process of German Patent No. DT 25 13 251 A1. For two component fibers, the polymers may be present in ratios of 75/25, 50/50, 25/75 or any other desired ratios. The fibers may also have shapes such as those described in U.S. Pat. Nos. 5,277,976 to Hogle et al., 5,466,410 to Hills and 5,069,970 and 5,057,368 to Largman et al., which describe fibers with unconventional shapes.

As used herein the term "blend" means a mixture of two or more polymers while the term "alloy" means a sub-class of blends wherein the components are immiscible but have been compatibilized.

As used herein, "ultrasonic bonding" means a process performed, for example, by passing the fabric between a sonic horn and anvil roll as illustrated in U.S. Pat. No. 4,374,888 to Bomslaeger.

As used herein "thermal point bonding" involves passing a fabric or web of fibers to be bonded between a heated calender roll and an anvil roll. The calender roll is usually, though not always, patterned in some way so that the entire fabric is not bonded across its entire surface, and the anvil roll is usually flat. As a result, various patterns for calender rolls have been developed for functional as well as aesthetic reasons. One example of a pattern has points and is the Hansen Pennings or "H&P" pattern with about a 30% bond area with about 200 bonds/square inch as taught in U.S. Pat. No. 3,855,046 to Hansen and Pennings. The H&P pattern has square point or pin bonding areas wherein each pin has a side dimension of 0.038 inches (0.965 mm), a spacing of 0.070 inches (1.778 mm) between pins, and a depth of bonding of 0.023 inches (0.584 mm). The resulting pattern has a bonded area of about 29.5%. Another typical point bonding pattern is the expanded Hansen Pennings or "EHP" bond pattern which produces a 15% bond area with a square pin having a side dimension of 0.037 inches (0.94 mm), a pin spacing of 0.097 inches (2.464 mm) and a depth of 0.039 inches (0.991 mm). Another typical point bonding pattern designated "714" has square pin bonding areas wherein each pin has a side dimension of 0.023 inches, a spacing of 0.062 inches (1.575 mm) between pins, and a depth of bonding of 0.033 inches (0.838 mm). The resulting pattern has a bonded area of about 15%. Yet another common pattern is the C-Star pattern which has a bond area of about 16.9%. The C-Star pattern has a cross-directional bar or "corduroy" design interrupted by shooting stars. Other common patterns include a diamond pattern with repeating and slightly offset diamonds with about a 16% bond area and a wire weave pattern looking as the name suggests, e.g. like a window screen, with about a 19% bond area. Typically, the percent bonding area varies from around 10% to around 30% of the area of the fabric laminate web. As is well known in the art, the spot bonding holds the laminate layers together as well as imparts integrity to each individual layer by bonding filaments and/or fibers within each layer.

As used herein, the terms "necking" or "neck stretching" interchangeably refer to a method of elongating a nonwoven fabric, generally in the machine direction, to reduce its width in a controlled manner to a desired amount. The controlled stretching may take place under cool, room temperature or greater temperatures and is limited to an increase in overall dimension in the direction being stretched up to the elongation required to break the fabric, which in most cases is about 1.2 to 1.4 times. When relaxed, the web retracts toward its original dimensions. Such a process is disclosed, for example, in U.S. Pat. Nos. 4,443,513 to Meitner and Notheis, 4,965,122, 4,981,747 and 5,114,781 to Morman and 5,244,482 to Hassenboehler Jr. et al.

As used herein the term "neck softening" means neck stretching carried out without the addition of heat, i.e. at ambient temperature, to the material as it is stretched in the machine direction. In neck stretching or softening, a fabric is referred to, for example, as being stretched by 20%. This means it is stretched in the machine direction until its width is 80% of its original unstretched width.

As used herein, the term "neckable material" means any material which can be necked.

As used herein, the term "necked material" refers to any material which has been constricted in at least one dimension by processes such as, for example, drawing or gathering.

As used herein the term "un-necking" means a process applied to a reversibly necked material to extend it by the application of a stretching force in a direction generally perpendicular to the direction of the original stretching force which causes it to recover to within at least about 50 percent of its reversibly necked dimensions upon release of the stretching force.

As used herein, the term "wash softened" refers to the feel of a material that has been softened by washing in a conventional home-type washing machine.

As used herein, the terms "elastic" and "elastomeric" when referring to a fiber, film or fabric mean a material which upon application of a biasing force, is stretchable to a stretched, biased length which is at least about 150 percent, or one and a half times, its relaxed, unstretched length, and which will recover at least 50 percent of its elongation upon release of the stretching, biasing force.

As used herein the term "recover" refers to a contraction of a stretched material upon termination of a biasing force following stretching of the material by application of the biasing force. For example, if a material having a relaxed, unbiased length of one (1) inch was elongated 50 percent by stretching to a length of one and one half (1.5) inches the material would have a stretched length that is 150 percent of its relaxed length. If this exemplary stretched material contracted, that is recovered to a length of one and one tenth (1.1) inches after release of the biasing and stretching force, the material would have recovered 80 percent (0.4 inch) of its elongation.

As used herein, the term "garment" means any type of non-medically oriented apparel which may be worn. This includes industrial work wear and coveralls, undergarments, pants, shirts, jackets, gloves, socks, and the like.

As used herein, the term "infection control product" means medically oriented items such as surgical gowns and drapes, face masks, head coverings like bouffant caps, surgical caps and hoods, footwear like shoe coverings, boot covers and slippers, wound dressings, bandages, sterilization wraps, wipers, garments like lab coats, coveralls, aprons and jackets, patient bedding, stretcher and bassinet sheets, and the like.

As used herein, the term "personal care product" means diapers, training pants, absorbent underpants, adult incontinence products, and feminine hygiene products.

TEST METHODS

Cup Crush: The softness of a nonwoven fabric may be measured according to the "cup crush" test. The cup crush test evaluates fabric stiffness by measuring the peak load (also called the "cup crush") required for a 4.5 cm diameter hemispherically shaped foot to crush a 23 cm by 23 cm piece of fabric shaped into an approximately 6.5 cm diameter by 6.5 cm tall inverted cup while the cup shaped fabric is surrounded by an approximately 6.5 cm diameter cylinder to maintain a uniform deformation of the cup shaped fabric. An average of 10 readings is used. The foot and the cup are aligned to avoid contact between the cup walls and the foot which could affect the readings. The peak load is measured while the foot is descending at a rate of about 0.25 inches per second (380 mm per minute) and is measured in grams. The cup crush test also yields a value for the total energy required to crush a sample (the "crush energy") which is the energy from the start of the test to the peak load point, i.e. the area under the curve formed by the load in grams on one axis and the distance the foot travels in millimeters on the other. Crush energy is therefore reported in gm-mm. Lower cup crush values indicate a softer fabric. A suitable device for measuring cup crush is a model FTD-G-500 load cell (500 gram range) available from the Schaevitz Company, Pennsauken, N.J.

The values reported in the Tables herein are cup crush load values.

DETAILED DESCRIPTION OF THE INVENTION

The object of the invention is achieved by a web of thermoplastic polymer fibers where the polymer used to form the web has an additive to enhance softening and the formed web is mechanically softened.

A number of softening chemicals are known in the art and generally include silicone in some form. Examples of silicone containing compounds are shown in U.S. Pat. No. 4,923,914 to Nohr and MacDonald for the purpose of increasing wettability of a web. Another suitable silicone containing compound is an ultra high molecular weight polymer available in solid pellet form as a family of polymers sold under the designation Dow Coming® MB50 Silicone Masterbatch polymer. One particular Dow Coming® MB50 Silicone Masterbatch polymer has about 50 percent silicone content and an organic resin of a 12 melt index polypropylene and is designated Dow Coming® MB50-001 Silicone Masterbatch polymer. The family of Dow Coming® MB50 Silicone Masterbatch polymers is available from the Dow Coming Corporation of Midland, Mich.

The preferred additive for the practice of this invention is of a particular class of siloxanes having the general formula:

wherein n is from 3 to about 1000.

One commercial source of a siloxane suitable for the practice of this invention is Dow Corning Corporation of Midland, Mich., which market the siloxane under the trade name 200® fluid. Other sources include General Electric, PPG Industries, Inc., Goldschmidt and OSi.

In order to practice this invention, the additive must be thoroughly mixed with the thermoplastic polymer. The mixture may be produced by compounding the ingredients in, for example, a 30 or 60 mm twin screw extruder. Any other method known to those skilled in the art of compounding polymers as effective may also be used. In the following Examples having internal additives, the mixture was produced by mixing the polymer, generally polypropylene, with each additive at a predetermined level in a twin screw extruder. The resulting polymer mixture was then dry blended with neat polymer in order to reach the percentage of additive mentioned in each Example.

The inventors have found for siloxane additives that amounts should be below 3 weight percent since amounts above this level have a negative effect on bonding. They have also found that the siloxane additive tends to migrate or bloom to the surface of the fiber, providing a degree of lubrication. The bulk softening and surface lubricity provided by the siloxane additive combined with mechanical softening results in a surprisingly softer and more drapable fabric in a commercially acceptable continuous process. The practice of this invention results in a fabric having a cup crush of at least 50% below a fabric produced without the combination of internal additive and mechanical treatment of this invention.

Mechanical treatment of a web may be carried out by a number of different methods such as micro creping, cold embossing, beater bar treatment, neckstretching, un-necking, and combinations thereof. Other methods known in the art may also be used.

Figure 1:
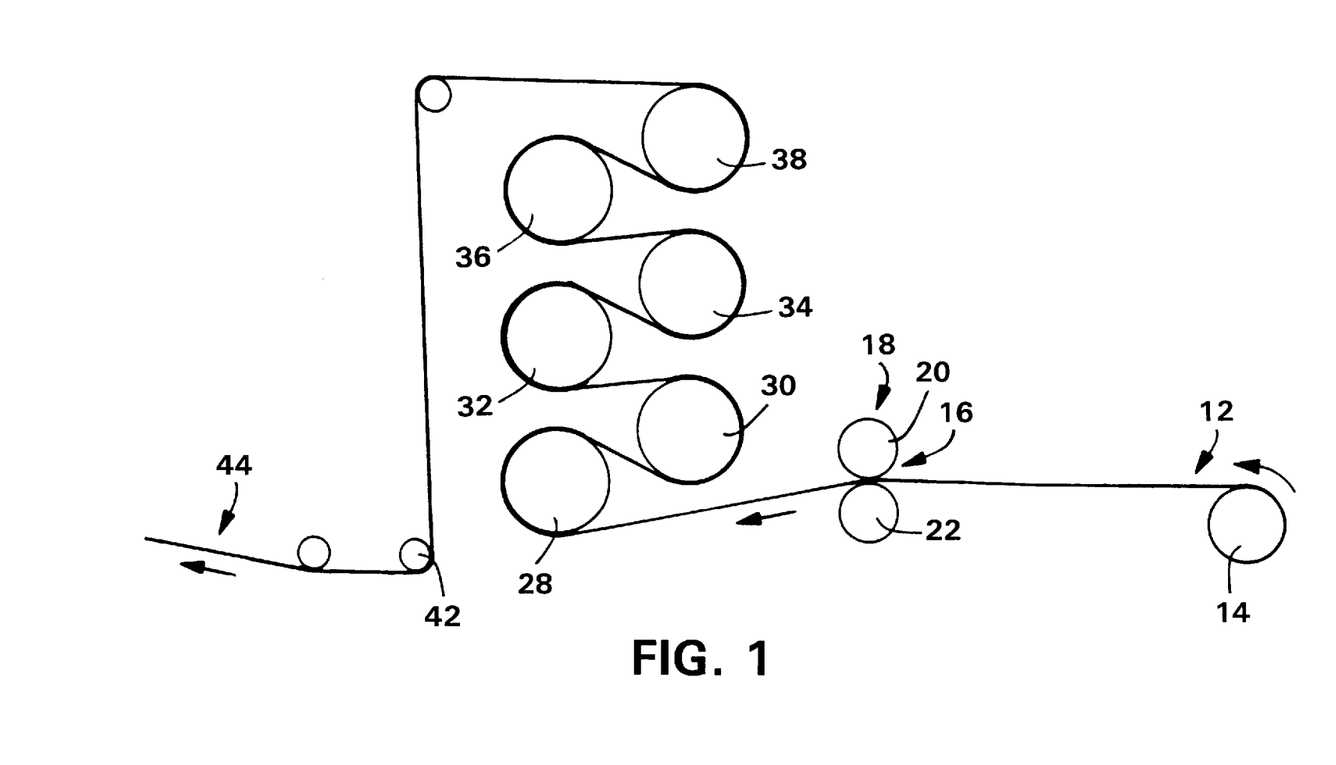
FIG. 1 is a schematic illustration of an apparatus which may be utilized to neck-stretch the fabric of the invention.

Turning to FIG. 1, in one embodiment of the present invention the neckable material 12 may be a multilayer material having, for example, at least one layer of spunbonded web joined to at least one layer of meltblown web, bonded carded web or other suitable material. For example, the neckable material 12 may be multilayer material having a first layer of spunbonded polypropylene having a basis weight from about 0.2 to about 8 ounces per square yard (osy), a layer of meltblown polypropylene having a basis weight from about 0.2 to about 4 osy, and a second layer of spunbonded polypropylene having a basis weight of about 0.2 to about 8 osy.

Alternatively, the neckable material 12 may be single layer of material such as, for example, a spunbonded web having a basis weight of from about 0.2 to about 10 osy or a meltblown web having a basis weight of from about 0.2 to about 8 osy.

The neckable material 12 may also be a composite or coformed material made of a mixture of two or more different fibers or a mixture of fibers and particulates. Such mixtures may be formed by adding fibers and/or particulates to a gas stream in which meltblown fibers are carried so that an intimate entangled commingling of meltblown fibers and other materials, e.g., wood pulp, staple fibers or particulates such as, for example, superabsorbent materials occurs prior to collection of the fibers upon a collecting device to form a coherent web of randomly dispersed meltblown fibers and other materials such as disclosed in U.S. Pat. No. 4,100,324 to Anderson et al.

If the neckable material 12 is a nonwoven web of fibers, the fibers should be joined by interfiber bonding to form a coherent web structure which is able to withstand necking. Interfiber bonding may be produced by entanglement between individual meltblown fibers. The fiber entangling is inherent in the meltblown process but may be generated or increased by processes such as, for example, hydraulic entangling or needlepunching. Alternatively and/or additionally a bonding agent may be used to increase the desired bonding or bonding may be accomplished by ultrasonic, print or thermal point bonding.

After passing through the nip 16 of the driver roller arrangement 18, the neckable material 12 passes over a series of steam cans 28-38 in a series of reverse S loops. The steam cans 28-38 typically have an outside diameter of about 24 inches although other sized cans may be used. The contact time or residence time of the neckable material on the steam cans to effect heat treatment will vary depending on factors such as, for example, steam can temperature, and type and/or basis weight of material. For example, a necked web of polypropylene may be passed over a series of steam cans heated to a measured temperature from room temperature to about 150° C. (302° F.) for a contact time of about 1 to about 300 seconds to effect heat treatment. More particularly, the temperature may range from about 100° C. to about 135° C. and the residence time may range from about 2 to about 50 seconds.

Because the peripheral linear speed of the drive rollers 20 and 22 is controlled to be lower than the peripheral linear speed of the steam cans 28-38, the neckable material 12 is tensioned between the steam cans 28-38 and the drive rollers 20 and 22. By adjusting the difference in the speeds of the rollers, the neckable material 12 is tensioned so that it necks a desired amount from a first, starting, un-necked width to a second width and is maintained in such necked condition while passing over the heated steam cans 28-38. This action imparts memory of the necked condition to the neckable material 12. The peripheral linear speed of the rollers of the idler roller arrangement 42 may be maintained at a higher speed then the steam cans 28-38 so that the necked material 12 is further stretched and also cooled in the necked condition on its way to the un-necking step of FIG. 2. This completes formation of the reversibly necked material 44.

Figure 2:
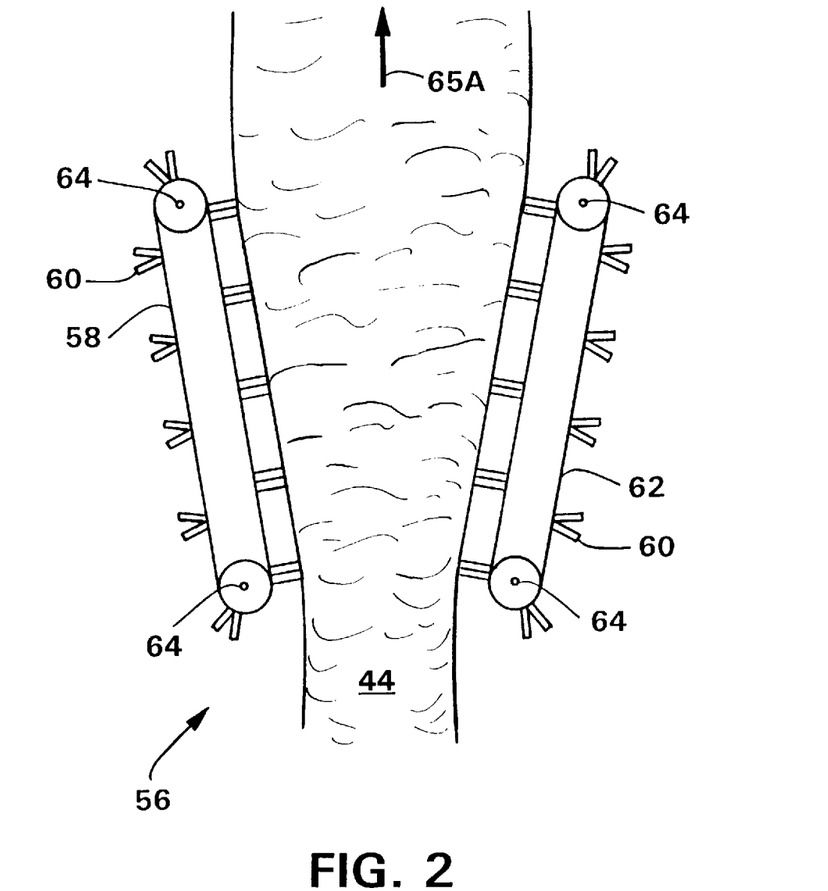
FIG. 2 is an illustration of an apparatus which may be used to un-neck the fabric of the invention.

The reversibly necked material 44 can be extended to a third width which is about its original, pre-necked dimensions upon application of a stretching force in a generally cross-machine direction. Un-necking of a fabric is accomplished through the use of commercially available devices such as Tenter frames which grab the edges of the fabric and pull it to the desired width, and which are shown in FIG. 2. In the practice of this type of un-necking device, the reversibly necked material 44 is passed to the unnecking assembly 56, comprising a Tenter frame, which is known to those skilled in the art. FIG. 2 shows a Tenter frame in which a chain 58 having a plurality of clips 60 attached to the chain links and spaced along the chain 58, and a chain 62 having clips 60 similarly spaced therealong. The chains 58 and 62 are actuated by gears 64 which are driven by a motor 65 (not shown). The chains 58 and 62 are not parallel, rather they diverge (from a top view) in the downstream direction (indicated by arrow 65A). As the material 44 approaches the assembly 56 the open clips 60 automatically and sequentially close and grip the edge of the laminate. As the chains 58 and 62 advance, the material 44 is stretched as the chain paths diverge. As the clips 60 reach the end of the top of the chain run, the clips automatically open, releasing the stretched fabric 44. The material can then recover to within at least about 50 percent of its reversibly necked dimensions upon release of the stretching force. The finished formed fabric 44 may be wound onto a roll (not shown) for uptake and storage.

An absolute cup crush load value of about 70 grams or less is considered desirably soft for the purposes of this invention. Fabrics processed according to this invention have a final cup crush load value of at least 50 percent less than the starting cup crush value of such a fabric, i.e., the final cup crush load value is no more than 50% of the starting cup crush load value. In addition, the various treatment methods discussed herein, including the instant invention, are not as effective on lighter basis weight fabrics since they already have low cup crush values by virtue of their thinness and inherent conformability. Basis weights above about 1 osy (34 gsm) are the ones most affected by the treatment methods discussed below and are the predominate area of applicability of the invention.

The inventors further believe that a web treated with an internal softener and mechanical treatment as described herein would also benefit from a topical treatment if desired. For example, the topical treatments as described in U.S. Pat. No. 5,413,811 to Fitting et al. would probably function to lower the web cup crush still further. In Fitting, the softening chemicals are added in an amount of between 0.1 and 10 weight percent of the nonwoven web prior to mechanical softening. These chemicals may be any of those commonly known to those skilled in the art as being useful for softening textiles. Softeners may be silicone, anionic, nonionic or cationic though cationic softeners are preferred.

Anionic softeners are generally chemical compounds such as sulfated oils like castor, olive and soybean, sulfated synthetic fatty esters, such as glyceryl trioleate, and sulfated fatty alcohols of high molecular weight.

Nonionic softeners are highly compatible with other finishing agents and are generally compounds such as glycols, glycerin, sorbitol and urea. Compounds of fatty acids like polyglycol esters of high molecular weight saturated fatty acids such as palmitic and stearic acids are other examples.

Cationic softeners are generally long chain amides, imidazolines, and quaternary nitrogen compounds. One suitable cationic softener is a tallow based quaternary ammonium compound sold under the tradename Varisoft®. Textile softeners are discussed in Textile Laundering Technology (1979), Riggs, C. L., and Sherill, J. C. (p. 71–74), the magazine American Dyestuff Reporter, September 1973 (p. 24–26) and the magazine Textile World, December 1973 (p. 45–46).

The following examples show the effect of various treatment methods on the cup crush values of nonwoven material. Note that because of the standard deviation of the cup crush test, each data point represents the measurement of at least five individual fabrics. Note also that only Example 8 has examples of the invention.

EXAMPLE 1

A nonwoven spunbond-meltblown-spunbond (SMS) laminate was made generally according to U.S. Pat. No. 4,041,203 in which the layers were sequentially deposited onto a moving forming wire. The layers were respectively 0.5-0.5-0.5 osy (17-17-17 gsm) for a 1.5 osy (51 gsm) total basis weight for the laminate. The polymers used to produce the layers were respectively, PF-304 available from the Himont Corporation, 3795G available from the Exxon Chemical Company, and PF-304. The laminate was thermally point bonded to produce a coherent nonwoven web.

In this example the laminates were washed in a conventional home-type washing machine. The wash cycle was 30 minutes long and used warm water and ½ cup of Tide® detergent. In the samples which were washed more than once, more detergent was added after each wash and the next wash cycle begun without drying between cycles. After all of the wash cycles were completed, each sample was put into a conventional home-type dryer on the low setting for 30 minutes. The SMS laminates were then tested for cup crush values and the results are reported in Table 1.

TABLE 1

| Sample | Control | Sample | % change |
|---|---|---|---|
| 1.5 osy SMS | 205 | same | NA |
| 1.5 osy SMS washed 1 time | 205 | 70 | −66 |
| 1.5 osy SMS washed 5 times | 205 | 50 | −76 |

The results clearly show the dramatic increase in softness attributable to mechanical softening through washing alone. Not only does washing result in a great decrease in the cup crush value in percentage terms, but the absolute value of the cup crush indicates a very soft fabric.

Washing is, unfortunately, a very water, labor, and energy intensive method for softening a nonwoven fabric. Washing is a batch process which is not well suited to the continuous production of large volumes of fabric.

EXAMPLE 2

A nonwoven spunbond-meltblown-spunbond (SMS) laminate was made generally according to U.S. Pat. No. 4,041,203 in which the layers were sequentially deposited onto a moving forming wire. The layers were respectively 0.55-0.5-0.55 osy (19-17-19 gsm) for a 1.6 osy (54 gsm) total basis weight for the laminate. The polymers used to produce the layers were the same as in Example 1 above. The laminate was thermally point bonded to produce a coherent nonwoven web.

In this example, the laminates were neck softened to a width of 80% of the starting, unstretched width (i.e., by 20%). The SMS laminates were then tested for cup crush values and the results are reported in Table 2.

TABLE 2

| Sample | Control | Sample | % change |
|---|---|---|---|
| 1.6 osy SMS, not neck softened | 295 | same | NA |
| 1.6 osy SMS, 20% neck softened | 295 | 243 | −18 |

The results show that neck softening can reduce the cup crush of a nonwoven fabric by a significant amount.

EXAMPLE 3

A nonwoven spunbond-meltblown-spunbond (SMS) laminate the same as that of Example 2 was used for this example.

In this example, the laminates were neck stretched by the percent of the starting, unstretched width as shown in Table 3 and at between 230° and 250° F. (110° and 121° C.). The SMS laminates were then tested for cup crush values and the results are shown in Table 3.

TABLE 3

| % necking | Control | Sample | % change |
|---|---|---|---|
| 0 | 180 | same | NA |
| 20 | 180 | 140 | −22 |
| 30 | 180 | 120 | −33 |
| 40 | 180 | 116 | −36 |
| 45 | 180 | 105 | −42 |
| 50 | 180 | 94 | −48 |

The results show that neck stretching can decrease the cup crush in amounts roughly proportional to the amount of neck stretching. The absolute cup crush values, however, were far above the results of mechanical washing alone.

EXAMPLE 4

A nonwoven spunbond-meltblown-spunbond (SMS) laminate the same as Example 1 was used for this example.

In this example, the laminates were topically treated with two softening chemicals. The chemicals were Y-12230 which is a polyalkyleneoxide modified polydimethyl siloxane and is commercially available from OSi (formerly a division of Union Carbide Corp.) of Danbery, Conn., and Triton® X-405, an alkylaryl polyether alcohol, available from the Rohm & Haas Company of Philadelphia, Pa. The chemicals were mixed with water to produce an aqueous solution containing the weight percent of the chemical as shown in Table 4. The treatment was applied to the webs by the "dip and squeeze" method described above, though alternatives like spraying would also function. The SMS laminates were then tested for cup crush values and the results are reported in Table 4.

TABLE 4

| Sample | Control | Sample | % change |
|---|---|---|---|
| 1.5 osy SMS, not treated | 205 | same | NA |
| 1.5 osy SMS, 0.5% Y-12230 | 205 | 179 | −13 |
| 1.5 osy SMS, 0.3% Triton ® X-405 | 205 | 161 | −21 |

The results show that certain topical chemical treatments alone can reduce the cup crush of a nonwoven fabric by about 15 to 20%.

EXAMPLE 5

A nonwoven spunbond-meltblown-spunbond (SMS) laminate the same as Example 2 was used for this example.

In this example, the laminates were neck stretched by 30% at a temperature of 230° F. (110° C.) and then treated with three different softening chemicals. In the Table (5), the first two lines show the results for the base fabric without neck stretching (N.S.) or treatment and for only neckstretching, respectively. The chemicals used were Y-12230, Triton® X-405, and Ultralube®, a proprietary surfactant hydrocarbon blend, which is available from MFG Chemical and Supply, Inc. of Dalton Ga. The chemicals were mixed with water to produce an aqueous solution containing the weight percent of the chemical as shown in Table 5. The treatment was applied to the webs by the "dip and squeeze" method described above, though alternatives like spraying would also function. The SMS laminates were then tested for cup crush values and the results are reported in Table 5.

TABLE 5

| Sample | Control | Sample | % change |
|---|---|---|---|
| Not N.S., not treated | 226 | same | NA |
| 30% N.S., not treated | 226 | 114 | −50 |
| 30% N.S. then 1.0% Y-12230 | 226 | 119 | −47 |
| 30% N.S. then 1.0% Triton ® X-405 | 226 | 143 | −37 |
| 30% N.S. then 1.0% Ultralube ® | 226 | 156 | −31 |

The results show that neck stretching followed by certain topical chemical treatments can reduce the cup crush of a nonwoven fabric up to about 50%. The absolute cup crush values, however, were far above the results of mechanical washing alone.

EXAMPLE 6

A nonwoven spunbond-meltblown-spunbond (SMS) laminate the same as Example 1 was used for this example.

In this example, the laminates were treated with three different topical softening chemicals and then neck stretched by 30%, except for the final sample which was neck stretched by 40%, at a temperature of about 245° F. (118° C.). In the Table (6), the first line shows the results for the base fabric without neck stretching or treatment.

The topical softening chemicals used were Y-12230, Triton® X-405, and Varisoft® 137 which is available from Sherex Chemical Co. of Dublin, Ohio. Varisoft is a dihydrogenated tallow dimethyl ammonium methyl sulfate and has CAS number G8002-58-4. Hexanol is used as a co-surfactant for the Y-12230 and is driven off during the drying of the nonwoven so that it does not remain in any effective amount in the finished product. The chemicals were mixed with water to produce an aqueous solution containing the weight percent of the chemical as shown in Table 6. The treatment was applied to the webs by the "dip and squeeze" method described above, though alternatives like spraying would also function. The SMS laminates were then tested for cup crush values and the results are reported in Table 6.

TABLE 6

| Sample | Control | Sample | % change |
|---|---|---|---|
| Not treated, not N.S. | 226 | same | NA |
| 30% N.S. with 0.5% Y-12230 | 226 | 112 | −50 |
| 30% N.S. with 0.3% Triton ® X-405 | 226 | 110 | −52 |
| 30% N.S. with 1.0% Varisoft | 226 | 102 | −55 |
| 40% N.S. with 1.0% Varisoft, 0.5% Y-12230, and 0.5% hexanol (1.6 osy SMS) | 226 | 72 | −68 |

The results show that topical treatment with certain chemicals followed by neck stretching can reduce the cup crush of a nonwoven fabric up to about 70%, yielding an absolute cup crush value in the range of washed fabrics.

EXAMPLE 7

A nonwoven spunbond-meltblown-spunbond (SMS) laminate the same as Example 2 was used for this example.

In this example, the laminates were neck stretched in the amounts shown, at a temperature of about 230° to 250° F. (110° to 121° C.) and then un-necked to a width about 20% greater than their original width according to the procedure described above. In the Table (7), the first line shows the results for the base fabric without neck stretching, treatment or un-necking.

The topical treatment for those webs having treatment was applied to the webs by the "dip and squeeze" method described above, though alternatives like spraying would also function. The SMS laminates were then tested for cup crush values and the results are reported in Table 7.

TABLE 7

| Sample | Control | Sample | % change |
|---|---|---|---|
| Not treated, not N.S. | 180 | same | NA |
| 30% N.S. | 180 | 95 | −47 |
| 40% N.S. | 180 | 86 | −52 |
| 40% N.S. with 1.0% Varisoft, 0.5% Y-12230, and 0.5% hexanol | 180 | 51 | −72 |

The results show that topical treatment with certain chemicals followed by neck stretching and un-necking can reduce the cup crush of a nonwoven fabric about 70%, yielding an absolute cup crush value in the range of washed fabrics. This fabric and process are further described in U.S. Pat. No. 5,413,811 to Fitting et al.

EXAMPLE 8

A spunbond fabric was made having a basis weight of 1.2 osy (41 gsm) from a polypropylene polymer commercially available from Exxon Chemical and known as ESCORENE® PD-3445 polypropylene. The siloxane additive 200® fluid was mixed with the polymer prior to extrusion in amounts as shown in Table 8. The fabric was spun at 430° F. (221° C.) at a rate of approximately 0.6 grams/hole/minute. The fabric was bonded by thermal calendering at a pattern roll temperature of 280° F. (138° C.) using an expanded Hansen Pennings pattern with a 15% bond area as taught in U.S. Pat. No. 3,855,046 to Hansen and Pennings. Some of the samples were necksoftened by the amount shown in Table 8 at ambient temperature and then un-necked to approximately their pre-necksoftened width. The samples were then tested for cup crush and the results are reported in Table 8.

TABLE 8

| Sample | Control | Sample | % change |
|---|---|---|---|
| No additive, no N.S. | 149 | 149 | NA |
| 3% additive, no N.S. | 149 | 115 | −23 |
| 0% additive, 50% N.S. | 149 | 105 | −30 |
| 3% additive, 20% N.S. | 149 | 94 | −37 |
| 3% additive, 45% N.S. | 149 | 68 | −54 |
| 3% additive, 53% N.S. | 149 | 61 | −59 |

The results show that internal treatment with certain chemicals followed by neck stretching and un-necking can reduce the cup crush of a nonwoven fabric about 60%, yielding an absolute cup crush value in the range of washed fabrics. The inventors believe that this result will occur with SMS laminates as well.

The above example shows that a nonwoven fabric comparable in softness to a washed fabric can be produced through internal chemical and mechanical treatment in a continuous, commercially feasible operation. The resulting fabric, though soft, retains a sufficient amount of its original properties e.g.: strength, to be of use in a number of useful products. The internal treatment used in this invention is relatively simple to carry out in a manufacturing setting as it involves blending one additional ingredient into the polymer mix. The topical treatment of Example 7, while quite effective, is a relatively messy process involving additional equipment and process steps.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. In the claims, means plus function claims are intended to cover the structures described herein as performing the recited function and not only structural equivalents but also equivalent structures. Thus although a nail and a screw may not be structural equivalents in that a nail employs a cylindrical surface to secure wooden parts together, whereas a screw employs a helical surface, in the environment of fastening wooden parts, a nail and a screw may be equivalent structures.

It should further be noted that any patents, applications or publications referred to herein are incorporated by reference in their entirety.

What is claimed is:

1. A nonwoven web comprising a polymer and between a positive amount and about 3 weight percent of an internal softening agent having a formula consisting essentially of wherein n is from 3 to about 1,000, and which web has been mechanically softened wherein the web has a cup crush value which is less than 50 percent of a cup crush value of the same fabric without said internal additive and said mechanical softening.

2. The web of claim 1 wherein said mechanical softening is a method selected from the group consisting of micro-creping, cold embossing, beater bar treatment, neck stretching, un-necking and combinations thereof.

3. The web of claim 1 wherein said mechanical softening is neck stretching to a second width of between about 50 and 95 percent of its first, starting, unstretched width.

4. The web of claim 3 wherein said mechanical softening includes un-necking after said neck stretching, to a third width of between about 80 and 150 percent of its starting, unstretched width.

5. The web of claim 1 further comprising a topical softening treatment prior to said mechanical treatment.

6. The web of claim 1 wherein said polymer is selected from the group consisting of polyolefins, polyamides, polyetheresters and polyurethanes.

7. The web of claim 6 wherein said polymer is a polyolefin.

8. The web of claim 7 wherein said polyolefin is polypropylene.

9. The web of claim 7 wherein said polyolefin is polyethylene.

10. The web of claim 1 further comprising at least one meltblown layer and at least one spunbond layer.

11. The web of claim 10 wherein said web is a laminate comprising a first spunbond layer, a meltblown layer and a second spunbond layer, and which has been bonded together.

12. The web of claim 11 wherein said web has been thermally point bonded.

13. A garment comprising the fabric of claim 1.

14. A personal care product comprising the fabric of claim 1.

15. An infection control product comprising the fabric of claim 1.

16. A nonwoven web comprising a polymer and between a positive amount and about 3 weight percent of a siloxane softening agent having a formula consisting essentially of:

wherein n is from 3 to about 1000, and which web has been neck stretched to a second width of between about 50 and 95 percent of its starting, first, unstretched width and un-necked is to a third width of between about 80 and 150 percent of its starting, unstretched width and which has a cup crush value which is less than 50 percent of a cup crush value of the same fabric without said internal additive and said mechanical softening.

17. A medical gown comprising the fabric of claim 16.

* * * * *

UNITED STATES PATENT AND TRADEMARK OFFICE
CERTIFICATE OF CORRECTION

PATENT NO. : 5,770,531
DATED : June 23, 1998
INVENTOR(S) : Gregory T. Sudduth et al.

It is certified that error appears in the above-identified patent and that said Letters Patent is hereby corrected as shown below:

Column 4, Line 40, "Bomslaeger" should read -- Bornslaeger --
Column 6, Line 2, "worm" should read -- worn --
Column 6, Line 59, "Coming" should read -- Corning --
Column 6, Line 60, "Coming" should read -- Corning --
Column 6, Line 63, "Coming" should read -- Corning --
Column 6, Line 65, "Coming" should read -- Corning --
Column 6, Line 66, "Coming" should read -- Corning --
Column 7, Line 11, "Coming" should read -- Corning --

Signed and Sealed this

Fourth Day of January, 2000

Attest:

*Attesting Officer*

*Acting Commissioner of Patents and Trademarks*